United States Patent [19]
Kelly

[11] Patent Number: 5,132,227
[45] Date of Patent: Jul. 21, 1992

[54] MONITORING FORMALDEHYDE

[75] Inventor: Thomas J. Kelly, Worthington, Ohio

[73] Assignee: 35ttelle Memorial Institute, Columbus, Ohio

[21] Appl. No.: 517,875

[22] Filed: May 2, 1990

[51] Int. Cl.$^5$ .......................................... G01N 21/64
[52] U.S. Cl. .................... 436/130; 436/172; 422/68.1; 422/83; 422/88
[58] Field of Search ............... 436/130, 172; 422/88, 422/83, 68.1

[56] References Cited

U.S. PATENT DOCUMENTS 4,372,747  2/1983  Gabbay et al. .................... 436/67

FOREIGN PATENT DOCUMENTS 1242776  7/1986  U.S.S.R. ........................ 436/130

OTHER PUBLICATIONS

Okayama, A, "Fluorometric Determination of Urinary δ-Aminolevulinic Acid by High Performance Liquid Chromatography and Post-Column Derivatization", *J. Chrom.*, vol. 426, pp. 365-369, 1988.

Lazrus, A. L., et al., "Automated Fluorometric Determination of Formaldehyde in Air", *Analytical Chemistry*, vol. 60, No. 10, p. 1075, May 15, 1988.

Beasley, R. K. et al., "Sampling of Formaldehyde in Air With Coated Solid Sorbent and Determination by High Performance Liquid Chromatography", *Analytical Chemistry*, vol. 52, No. 7 pp. 1110-1114, 1980.

Primary Examiner—Robert J. Warden
Assistant Examiner—stephanie Blythe
Attorney, Agent, or Firm—Philip M. Dunson

[57] ABSTRACT

Methods and apparatus for monitoring formaldehyde vapor in a gas, comprising directing the gas into contact with an aqueous acidic solution that can dissolve the vapor and thus collect it therein, separating the gas from the solution, reacting the solution with a reagent to form from the collected formaldehyde a derivative that can be excited by radiation at a wavelength in the range of about 230 to 300 (typically 254) nanometers to fluoresce at a substantially different wavelength, irradiating the solution at a wavelength in said range for excitation, and measuring the intensity of the resulting fluorescence. Typically the fluorescence is measured at a wavelength in the range of about 450 to 550 nanometers and the irradiation and the measurement of fluorescence are carried out by means comprising conventional fluorometric means.

22 Claims, 5 Drawing Sheets

The Hantzsch Reaction

FIG. 6

1) Excitation Spectrum
2) Absorption Spectrum

Emission Spectrum

MONITORING FORMALDEHYDE

This invention was made with Government support under Contract 68-02-4127 awarded by the United States Environmental Protection Agency. The Government has certain rights in the invention.

FIELD

This invention relates to monitoring formaldehyde vapor in an aqueous solution or in a gas, and is especially useful for real-time measurement of formaldehyde vapor in air.

A typical monitor according to the present invention employs collection of formaldehyde in an aqueous solution, derivatization, and fluorescence detection of the derivative. The sensitivity of the aqueous fluorescence measurement is improved by using intense 254 nanometer light from a mercury lamp for excitation, rather than the 410 nanometer light used previously by others. The increased sensitivity of the aqueous analysis allows the use of a much simpler and more reliable collection device for gaseous formaldehyde than those used previously. The end result is a continuous real-time monitor for formaldehyde having sensitivity sufficient to measure concentrations in ambient air, and providing more stable and reliable performance than previous approaches.

BACKGROUND

The following disclosure includes (minimally edited) the paper by Thomas J. Kelly, Russel H. Barnes, and William A. McClenny, Real-time Monitors for Characterization of Formaldehyde in Ambient and Indoor Air, Proceedings of the 1989 EPA/A&WMA International Symposium, Measurement of Toxic and Related Air Pollutants; Raleigh, N.C., May, 1989, pp. 43-50. Air & Waste Management Association Publication VIP-13; EPA Report No. 600/9-89-060. [Portions enclosed in brackets do not relate directly to the present claimed invention.]

In this paper, the design considerations for two types of prototype gaseous formaldehyde monitors are reviewed and the experimental results of preliminary testing are discussed. The prototypes are designed to measure single digit ppbv to sub-ppbv (parts per billion volume) concentration levels in indoor and ambient outdoor environments. [One unit uses gas phase fluorescence for formaldehyde detection. For this approach, a commercially available monitor, originally designed for detection of sulfur dioxide, was altered by replacement of optical components and adjustment of other design features. Theoretical considerations indicate that this approach should be successful in achieving the desired level of detection sensitivity and selectivity for formaldehyde.] A second prototype was based on an improved design of a system using a wet scrubber for selective sampling of formaldehyde followed by an analytical procedure using the Hantzsch method; that is, cyclization of a β-diketone, an amine, and formaldehyde to form a dihydropyridine derivative which can be detected by fluorescence. Design options were considered including the choice of excitation wavelength and optical components for fluorescence detection.

Formaldehyde (HCHO) is the most abundant aldehyde in the ambient atmosphere, originating both from primary emissions in combustion sources and from atmospheric oxidation of hydrocarbons. Formaldehyde produces free radicals upon photolysis, contributing to the formation of ozone and other oxidants. Concentrations of formaldehyde in the ambient atmosphere range from below 1 ppbv in rural areas to several tens of ppbv in urban areas such as the Los Angeles basin. [1–5] A pronounced diurnal variation is observed in Los Angeles [2] due to the impact of both local sources and photochemistry, and a pronounced seasonal variation is observed in rural areas [3] due to seasonal changes in photochemical activity. Formaldehyde is also found in indoor air, originating from a variety of products. A national database on concentrations of volatile organic compounds [4] indicates that indoor formaldehyde concentrations are typically several times higher than outdoor concentrations. In either indoor or outdoor air, the presence of formaldehyde is important because of the toxicity of this chemical, including suspected carcinogenesis in humans.

Because of the importance of gaseous formaldehyde from both an atmospheric chemistry and a toxicology viewpoint, several methods have been developed for measurement of formaldehyde in air, and intercomparisons of methods have recently been performed. [2,5] Spectroscopic methods include Fourier transform infrared absorption (FTIR), differential optical absorption spectroscopy (DOAS), and tunable diode laser absorption spectroscopy (TDLAS). All are capable of real-time HCHO measurement, of importance in studying the short-term variations in ambient HCHO which convey information about its sources and sinks. However, all three spectroscopic devices are large, complex, and expensive, and only the TDLAS method appears to have sensitivity adequate for measurement of HCHO at the sub-ppbv levels characteristic of rural air. Smaller and less complex real-time HCHO detectors have also been developed, based on continuous collection of HCHO in aqueous solution for subsequent analysis by colorimetry, [e.g., 6] fluorescence, [7,8] or enzyme-catalyzed fluorescence. [9] These methods can provide high sensitivity, but they are subject to some operational difficulties. [2,10,11] Integrated collection and derivatization of HCHO with 2,4-dinitrophenyl-hydrazine [e.g., 3,11,12] can also provide high sensitivity but is not amenable to real-time analysis.

The purpose of the study was to develop new, sensitive, portable methods for real-time measurement of formaldehyde in air. Two methods have been developed to the prototype stage, one an improved wet scrubbing/fluorescence device, [the other a novel spectroscopic approach.]

After a survey of existing collection devices for gaseous HCHO, and a review of analytical approaches for HCHO in the aqueous phase, it appeared feasible to develop an improved HCHO monitor based on an aqueous scrubber with subsequent fluorescence analysis by the Hantzsch reaction, the cyclization of a β-diketone, an amine, and formaldehyde. [13] This analytical approach has been used previously, [7,8] employing a diffusion scrubber tube as the collection device for gaseous HCHO. Although the large air-to-water contact ratio provided by the scrubber allows sub-ppbv detection limits for gaseous HCHO, [7,8] the method suffers from the difficulty of assembling the diffusion scrubber and the very limited lifetime of the scrubber in continuous use. [2] However, we considered that improved analytical sensitivity for HCHO in the aqueous phase might allow use of a simpler and more reliable collection device, such as the glass coil used in another method for HCHO. [9] It appeared that such improvement in sensitivity might be possible by using the high intensity of the 254 nm Hg line for excitation of the fluorophore, [13] rather than the 410 nm excitation commonly used. [7,8] Thus the development of the wet chemical HCHO monitor followed the hypothesis that 254 nm excitation might provide improved sensitivity, thereby allowing use of a simpler and much more reliable collection device for gaseous HCHO.

The wet chemical HCHO monitor has been built around a Turner 112 fluorometer with a quartz HPLC fluorescence flow cell, and a Gilson Minipuls 2 peristaltic pump for circulation of scrubbing and reagent solutions. A glass 28-turn Autoanalyzer coil is used as the collector for gaseous HCHO, contacting a flow of 2 L/min air with 0.8 ml/min of 0.1N $H_2SO_4$ as scrubber solution. Reagent concentrations (ammonium acetate/acetic acid buffer, 2,4-pentanedione) are similar to those reported previously. [7] Standard UV lamps (G4 type) were compared as the excitation source to G4 and black-light lamps coated with a phosphor designed to emit maximally at 406 nm (BHK, Inc.); lamps coated with this phosphor were used in previous studies using this analysis method. [7,8]

[The spectroscopic method is based on gas-phase fluorescence detection of HCHO using UV excitation, an approach currently used to measure gaseous $SO_2$ in commercial devices. A review of literature in the area and extensive feasibility calculations indicated that direct gas-phase fluorescence should be a suitable method of HCHO detection. For practical reasons it was decided to assemble a prototype HCHO detector by modifications to a commercial fluorescence $SO_2$ detector. The commercial detector chosen to serve as the basis for the modifications is a Thermo Environmental Model 43-S; this detector was chosen because of its high sensitivity (detection limit for $SO_2$ about 0.1 ppbv) and excellent performance in field measurement programs. Feasibility calculations addressing the 43-S instrument indicated that HCHO detection could be achieved by three primary modifications to the 43-S: (1) changing excitation and emission filters to match the appropriate wavelengths for HCHO, (2) increasing the power output of the pulsed UV lamp, and (3) increasing the gain of the amplifier electronics. The first and third modifications have been performed on a 43-S instrument to produce our initial prototype. A gas-phase HCHO source based on decomposition of trioxane [14] has been assembled and used in initial testing of the prototype, as described below.]

CARRYING OUT THE INVENTION

Figure 1:
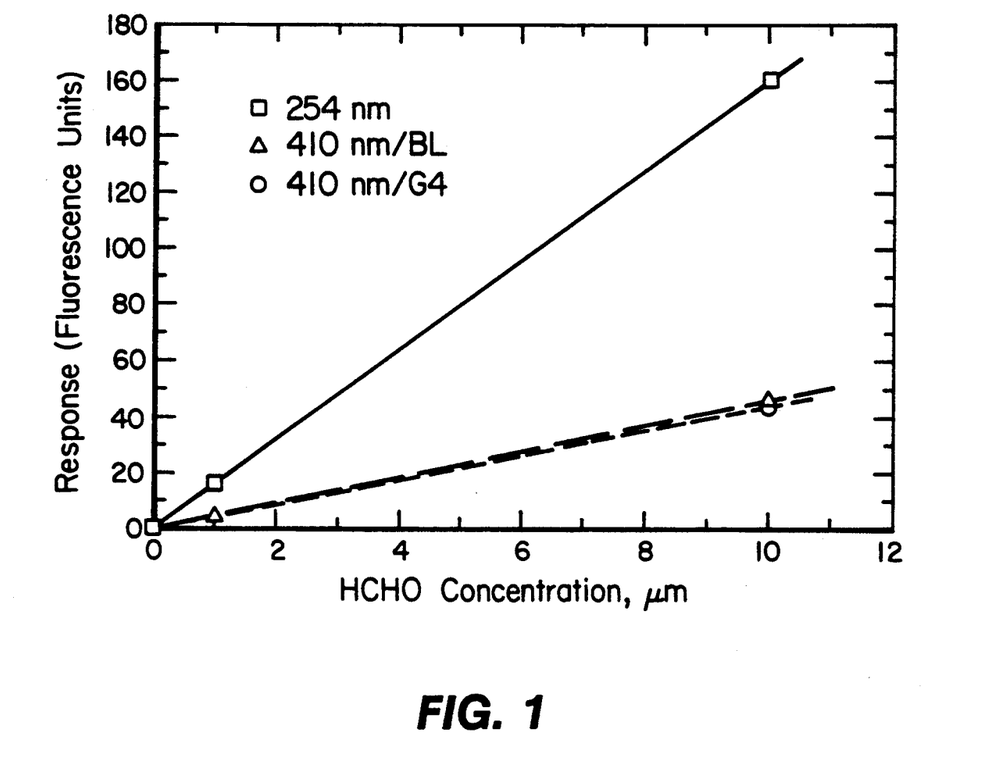
FIG. 1 is a graph of relative sensitivity of the wet chemical method for monitoring formaldehyde showing a comparison of the response in fluorescence units to excitation at 254 nanometers with response to excitation at 410 nanometers.
Figure 2:
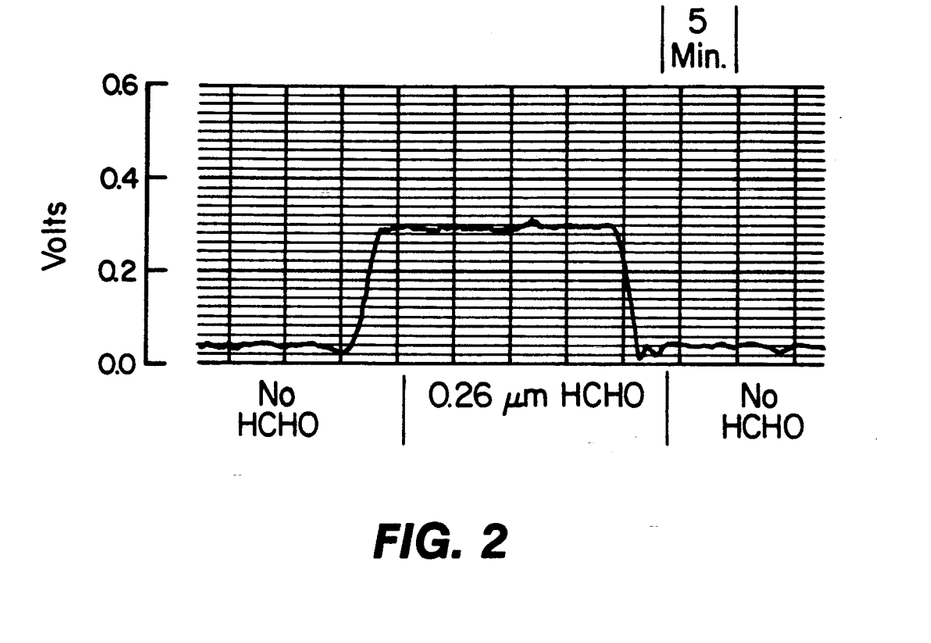
FIG. 2 is a graph showing response of the wet chemical monitor disclosed herein to 0.26 micromolar formaldehyde, which is equivalent to approximately 2.5 ppbv gaseous formaldehyde.

FIG. 1 shows a comparison of response to aqueous formaldehyde using 254 nm and 410 nm excitation. The sensitivity using 254 nm excitation is about 3.5 times as great as that using 410 nm excitation; as a result the former was used for all subsequent work. Note that the sensitivity obtained with the two kinds of phosphor-coated lamps is nearly identical, suggesting that the light output of the phosphor is saturated and thus not dependent on lamp type. The wet chemical HCHO monitor has been calibrated using both gaseous HCHO standards, from a porous Teflon tube source, and aqueous standards made by adding traces of HCHO to the 0.1N $H_2SO_4$ scrubbing solution. These two modes of calibration are equivalent because of the equilibration of phases and essentially complete collection of HCHO into the aqueous phase achieved in the glass coil scrubber. FIG. 2 shows the response of the device to 0.26 $\mu M$ HCHO in the scrubber solution while sampling zero air at the scrubber inlet. This concentration of HCHO is approximately the limit of detection of the fluorescence system developed previously using the Hantzsch reaction with 410 nm excitation. [7,8] However, as FIG. 2 shows, the detection limit of the present system is about 0.02 $\mu M$, or about an order of magnitude lower than that achieved in the previous work. This order of magnitude improvement is due partly to the higher sensitivity resulting from 254 nm excitation (FIG. 1), and partly from the fluorometer used in this study, which employs a large lamp and efficient optical design in the flowcell to maximize the intensity of excitation light reaching the sample.

Figure 3:
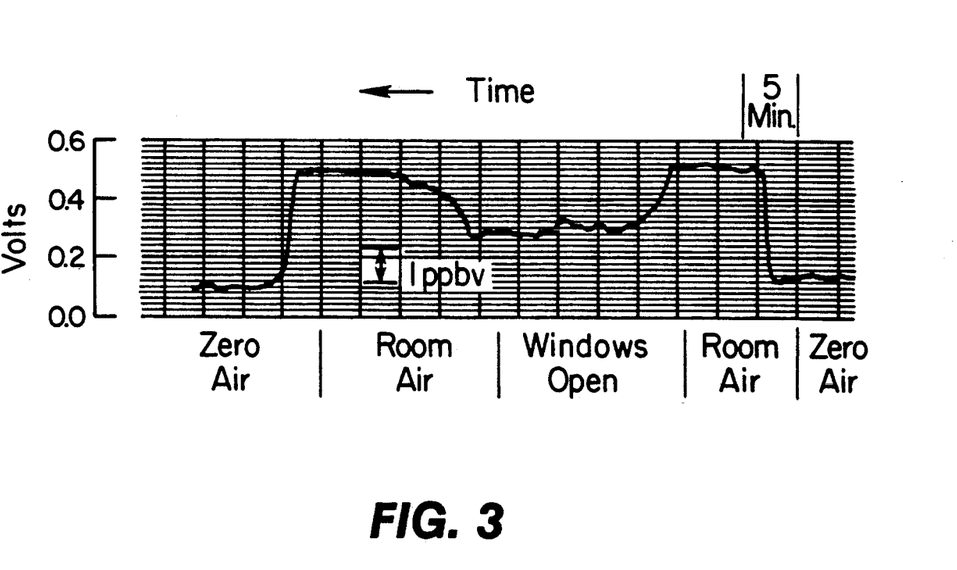
FIG. 3 is a graph similar to FIG. 2 showing typical measured response of the wet chemical method disclosed herein to gaseous formaldehyde in indoor and outdoor air.

The high sensitivity achieved in detection of aqueous HCHO translates into sensitive detection of gaseous HCHO using the simple but efficient glass coil scrubber. FIG. 3 shows measurements of gaseous HCHO in indoor and outdoor air. After an initial period of sampling zero air, the monitor was switched to sampling indoor air; a lag time of less than 2 minutes and a rise time of less than 1 minute were observed, and the response then stabilized at a concentration of about 3.5 ppbv. Opening the laboratory windows to flush the room with outside air resulted in a drop in observed HCHO concentration, and closing the windows resulted in a gradual return to the room air HCHO concentration. The response times observed for the present device are less than half those previously reported. [7] A gaseous detection limit of about 0.2 ppbv is indicated by FIG. 3; this is about a factor of two better than reported previously, [7] and is achieved with a simple and very reliable scrubber device.

Initial interference tests indicate that specificity of detection of HCHO is retained with the adoption of 254 nm excitation. Selectivity toward formaldehyde is greater than 10,000:1 relative to acetaldehyde, and greater than 2,000:1 relative to benzaldehyde.

Figure 4:
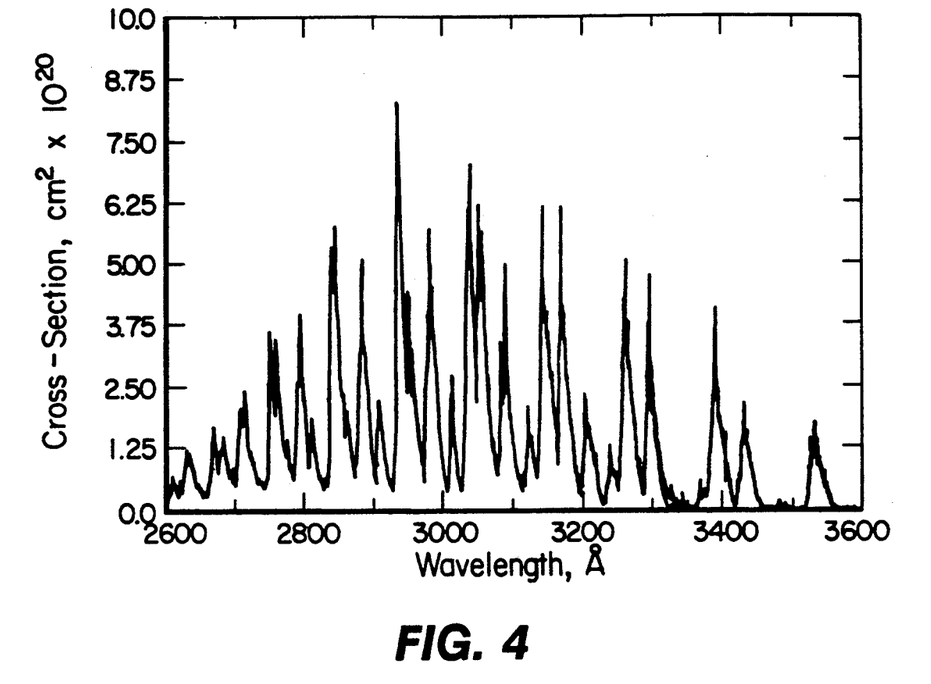
[FIG. 4 is a graph showing the absorption spectrum of formaldehyde for the region of fluorescence excitation from 2600 to 3600 angstroms.
Figure 5:
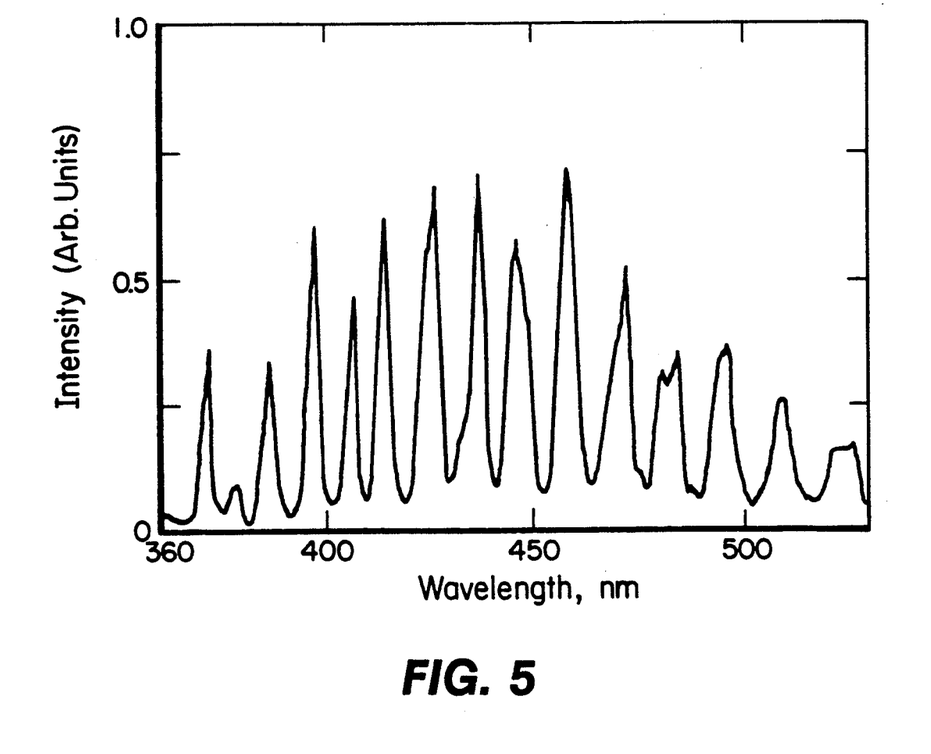
FIG. 5 is a graph showing the fluorescence spectrum from 360 to about 530 nanometers from formaldehyde in air at atmospheric pressure excited at 354.7 nanometers.]

[FIG. 4 shows the absorption region of HCHO used in the prototype spectroscopic monitor. HCHO fluorescence is excited in the prototype by wavelengths from about 300 to 360 nm encompassing several absorption bands. Excitation at shorter wavelengths leads largely to decomposition rather than to fluorescence. Note that excitation of $SO_2$ fluorescence in the unmodified 43-S occurs over wavelengths of 190–230 nm, thus the HCHO fluorescence is spectrally well separated from potential $SO_2$ interference. The HCHO fluorescence emission spectrum is shown in FIG. 5; maximum intensity occurs mainly in the region 400–450 nm.

The prototype HCHO monitor has been tested using the trioxane-based HCHO source. In these tests, a fluorescence background equivalent to about 6000 ppbv HCHO was observed in the absence of added formaldehyde. This background is believed to originate from fluorescence of the optical filters used in the prototype, and will be greatly reduced by improved filter selection. Despite the background observed, the prototype exhibited clear response to two calibration points of 1190 ppbv and 695 ppbv HCHO. Inspection of the instrument response indicates a detection limit for the prototype of less than 100 ppbv with a time response of less than 1 minute. These characteristics are considered very good given the early stage of development of the UV fluorescence detector. Additional avenues of possible improvement of the device, besides reducing the background, include increasing the lamp output, doubling the optical path of excitation light, improving collection of the fluorescence light, and optimizing the electronics.]

To Summarize: Two prototype monitors have been developed for real-time measurement of gaseous HCHO. One is an improved version of an existing wet scrubbing/fluorescence method. The improved monitor provides higher fluorescence sensitivity by means of UV excitation of the aqueous fluorophore, and as a result can employ a relatively simple and highly reliable collection device for gaseous HCHO. The detection limit of this device for aqueous formaldehyde is $2 \times 10^{-8}$M, and for gaseous formaldehyde is approximately 0.2 ppbv. [The second device employs gas-phase UV fluorescence detection for HCHO. The prototype of this device was assembled by modification of a highly sensitive commercial $SO_2$ detector. The UV fluorescence prototype exhibits a detection limit of less than 100 ppbv with time response of less than 1 minute.]

The following references are cited above, and are hereby incorporated by reference into this specification for purposes of indicating the background of the present invention and illustrating the state of the art.

REFERENCES

1. P. Carlier, H. Hannachi, and G. Mouvier, *Atmos. Environ.*, 20, 2079 (1986).
2. D. R. Lawson, H. W. Biermann, E. C. Tuazon, A. M. Winer, G. I. MacKay, H. I. Schiff, G. L. Kok, P. K. Dasgupta, and K. Fung, Formaldehyde measurement methods evaluation and ambient concentrations during the carbonaceous species methods comparison study, *Aerosol Sci. Technol.*, accepted (1989).
3. Z. Meng and R. L. Tanner, Rapid determination of ppbv levels of aldehydes in ambient air by high-performance liquid chromatography, Brookhaven National Laboratory Informal Report BNL-51725, Upton, N.Y., 55 pp (1983).
4. J. J. Shah and H. B. Singh, *Environ. Sci. Technol.*, 22, 1381 (1988).
5. T. E. Kleindienst, et al, *Atmos. Environ.*, 22, 1931 (1988).
6. R. R. Miksch, D. W. Anthon, L. Z. Fanning, C. D. Hollowell, K. Revzan, J. Glanville, *Anal. Chem.*, 53, 2118 (1981).
7. P. K. Dasgupta, S. Dong, H. Hwang, H.-C. Yang, and Z. Gensa, *Atmos. Environ.*, 22, 949 (1988).
8. S. Dong and P. K. Dasgupta, *Environ. Sci. Technol.*, 21, 581 (1987).
9. A. L. Lazrus, K. L. Fong, J. A. Lind, *Anal. Chem.*, 60, 1074 (1988).
10. P. E. Georghiou, L. Harlick, L. Winsor, D. Snow, *Anal. Chem.*, 55, 567 (1983).
11. M. W. Holdren, D. L. Smith, N. K. Russell, Investigation of 2,4-Dinitrophenyl-hydrazine Impregnated Adsorbent Tubes for the Collection of Airborne Aldehydes, Battelle Columbus Division Final Report to U.S. EPA, Contract 68-02-4127, Work Assignment 35, 43 pp (May, 1988).
12. D. Grosjean and K. Fung, *Anal. Chem.*, 54, 1221 (1982).
13. Belman, S., *Anal. Chim. Acta*, 29, 120 (1963).
14. Geisling, K. L., Miksch, R. R., Rappaport, S. M., *Anal. Chem.*, 54, 140 (1982).

The following disclosure includes portions of a FINAL REPORT on DEVELOPMENT OF REAL-TIME MONITORS FOR GASEOUS FORMALDEHYDE BY Thomas J. Kelly and Russell H. Barnes, BATTELLE, 505 King Avenue, Columbus, Ohio 43201-2693; Contract No. 68-02-4127, Work Assignments 58 and 70; Project Officer, William A. McClenny, Monitoring Methods Research Section, Methods Research Branch, Methods Research and Development Division, Atmospheric Research and Exposure Assessment Laboratory, U.S. Environmental Protection Agency, Research Triangle Park, N.C. 27711; Sep. 28, 1989. The entire report, including appendixes, is hereby incorporated by reference into this specification for purposes of indicating the background of the present invention and illustrating the state of the art.

The state of wet chemical methods for HCHO measurement was more advanced than that of spectroscopic methods at the beginning of this study, in the sense that portable, sensitive, real-time wet chemical methods did exist. However, the existing wet chemical methods all suffered from various difficulties or complexities, such that none was completely satisfactory. Development of a new wet chemical method began with a literature review of all existing methods for collection and analysis of gaseous HCHO. In conducting this review, collection devices and aqueous analytical methods were considered separately, under the assumption that in principle any collection device could provide a continuous aqueous stream for subsequent analysis. This approach was aimed at selecting independently the best scrubber and best analytical method, without adherence to the use of these approaches in previous work. The literature review disclosed four different aqueous analytical methods for HCHO, and eleven different designs of collection devices, falling into four design classes.

Figure 6:
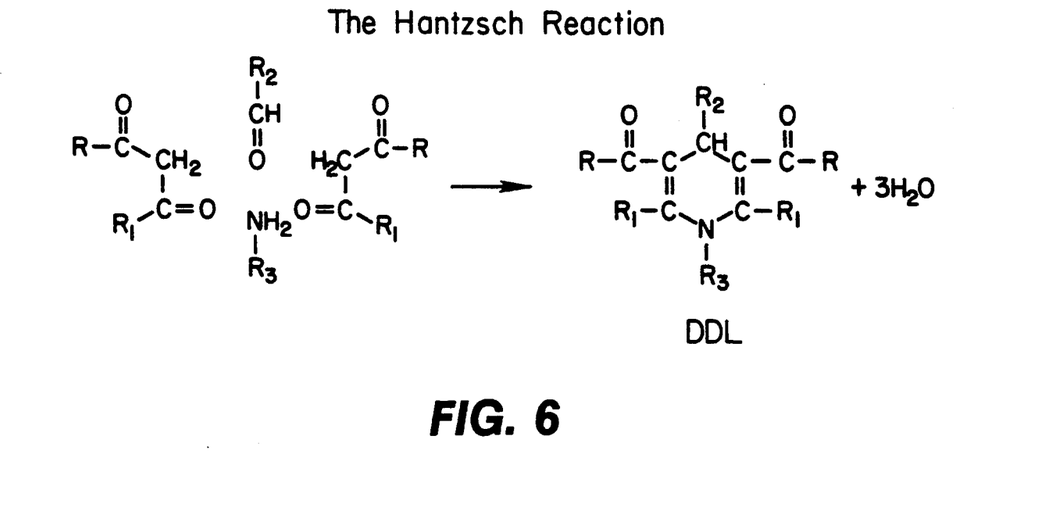
FIG. 6 is a schematic representation of the Hantzsch reaction, which is employed in methods according to the present invention.
Figure 7:
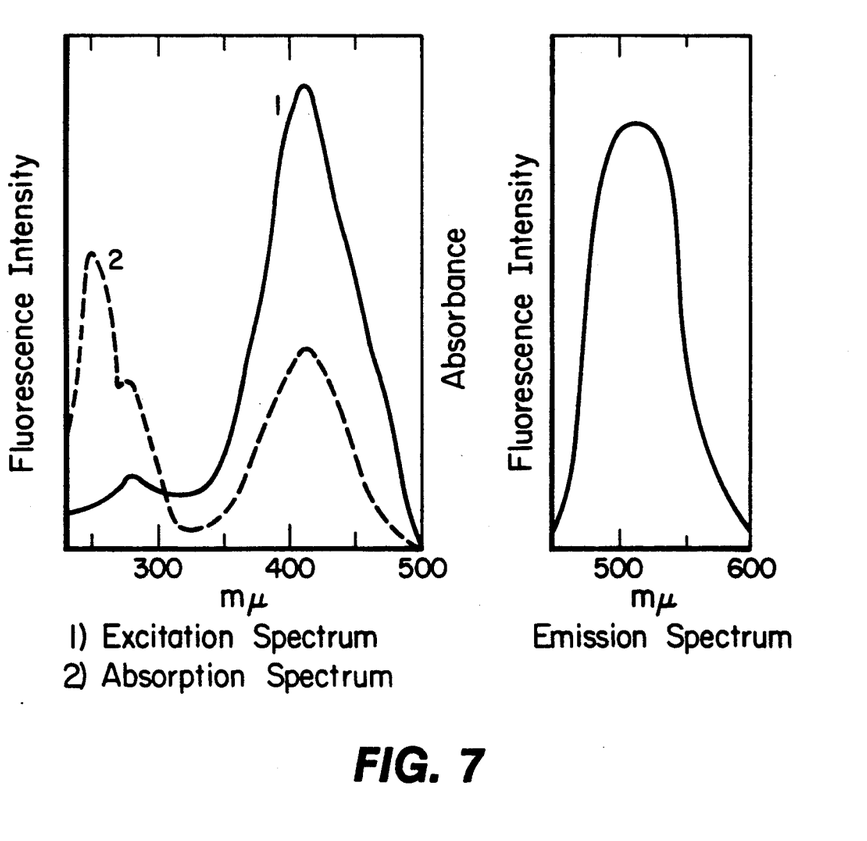
FIG. 7 is a graph of fluorescence intensity against wavelength showing the excitation, absorption, and emission spectra of DDL, the product of the Hantzsch reaction.

An evaluation of the four analytical methods concluded that the aqueous fluorescence method employing the Hantzsch reaction, the cyclization of a β-diketone, an aldehyde, and an amine, was the most attractive method for further development. FIG. 6 shows a simplified representation of the Hantzsch reaction, which actually occurs in several steps. This method uses common and inexpensive reagents, is sensitive, and highly selective towards formaldehyde. When 2,4-pentanedione and ammonium acetate are used as reagents (i.e., $R=R_1=CH_3$, $R_3=H$) the product formed is 3,5-diacetyl 1,4-dihydrolutidine (DDL). The DDL product is formed in 1:1 stoichiometry with formaldehyde, and is readily detected by fluorescence. This approach has been used previously for formaldehyde detection [13,7,8] with good results. However, it was concluded in the evaluation that the sensitivity of the method might be improved by use of 254 nm excitation from a mercury lamp [13], rather than the 410 nm excitation used previously [7,8]. For example, FIG. 7 shows the excitation, absorption, and fluorescence emission spectra of DDL, from Belman [13]. Note that the wavelength scales in FIG. 7 are labelled in mμ, which is equivalent to nm. These spectra indicate that absorption by DDL at 254 nm is considerably stronger than at 410 nm, but fluorescence appears to result primarily from 410 nm excitation, perhaps implying that 254 nm excitation leads largely to decomposition of the fluorophore. However, it was not entirely clear from the literature [13] whether the fluorescence behavior with 254 nm excitation had been well characterized, with the xenon lamp and optical system used in that study. Furthermore it seemed possible that the stronger absorption and very high light intensity available from a mercury lamp at 254 nm would result in overall higher fluorescence intensity despite the relative inefficiency of the fluorescence process. This potential for improvement in the method, as well as the existing capabilities of the method, made fluorescence using the Hantzsch reaction the aqueous analytical method of choice for this work.

In choosing a design for a collector of gaseous HCHO into the aqueous phase, the primary factor initially considered was the air/water contact ratio, i.e., the ratio of air and water volume flow rates in the collector. This ratio determines the concentrating effect of the collector, and impacts the ultimate sensitivity of the gas-phase measurement. However, in evaluating various scrubber designs it became apparent that many of the scrubbers offering high contact ratios were not adaptable to continuous measurements, or suffered from complexities which made them unattractive for a continuous instrument. The latter includes the porous tube scrubbers previously used with the Hantzsch reaction [7,8]. It was concluded that a glass coil concurrent flow scrubber design was the best collector for HCHO. This collector offers the advantages of high efficiency, simplicity, and reliability. It was anticipated that a real-time continuous instrument would benefit from the reliability of the coil scrubber, while improvements in aqueous sensitivity with the Hantzsch reaction would make up for the relatively low contact ratio of the scrubber.

Following selection of the collector and analysis approach to be used, the initial stage of development of a wet chemical formaldehyde monitor concluded with acquisition of the equipment needed to assemble the device. Equipment included a peristaltic pump, temperature controller, glassware, and a commercial fluorometer. The fluorometer (Turner Model 112) was selected because of its high sensitivity, quartz micro-volume flow cell, and efficient optical design. This fluorometer also allows rapid exchange of lamps and optical filter elements, of importance in testing various fluorescence approaches for use with the Hantzsch reaction.

The initial test planned for the wet chemical monitor was a comparison of sensitivity when using 254 nm excitation with that found when using 410 nm excitation [13]. The lowest background fluorescence was found with the combination of a GG-10 Schott glass filter (Corion, Inc.) and a 500 nm long-pass filter (Sequoia-Turner, Inc.) on the emission side of the fluorescence cell, with the Schott glass filter facing the cell. As a result, this filter combination was used for all subsequent work with 254 nm excitation.

After selection of the filter combination described above, the sensitivity comparison of 254 nm and 410 nm excitation was conducted. In this comparison reagent mixtures comparable to those used previously [7,8] were employed, spiked with micromolar concentrations of formaldehyde. A 254 nm line filter and the filter combination described above were used on the excitation and emission sides, respectively, for testing with the 254 nm excitation from a Hg lamp. For testing of 410 nm excitation, phosphor-coated lamps with peak emission at 406 nm (BHK, Inc.) were used, essentially identical to those used in existing HCHO detectors employing the Hantzsch reaction [7,8]. The excitation filter was a bandpass filter of central wavelength 410 n, with 10 nm spectral bandpass (Full Width at Half Maximum, FWHM) (Corion, Inc.) and the emission filter was a 470 nm cutoff long-pass filter (Sequoia-Turner). The results of this comparison are shown in FIG. 1, which indicates that 254 nm excitation provides approximately three times the sensitivity obtained with 410 nm excitation. As a result, it was concluded that 254 nm excitation would be used in further development of the wet chemical method.

Figure 8:
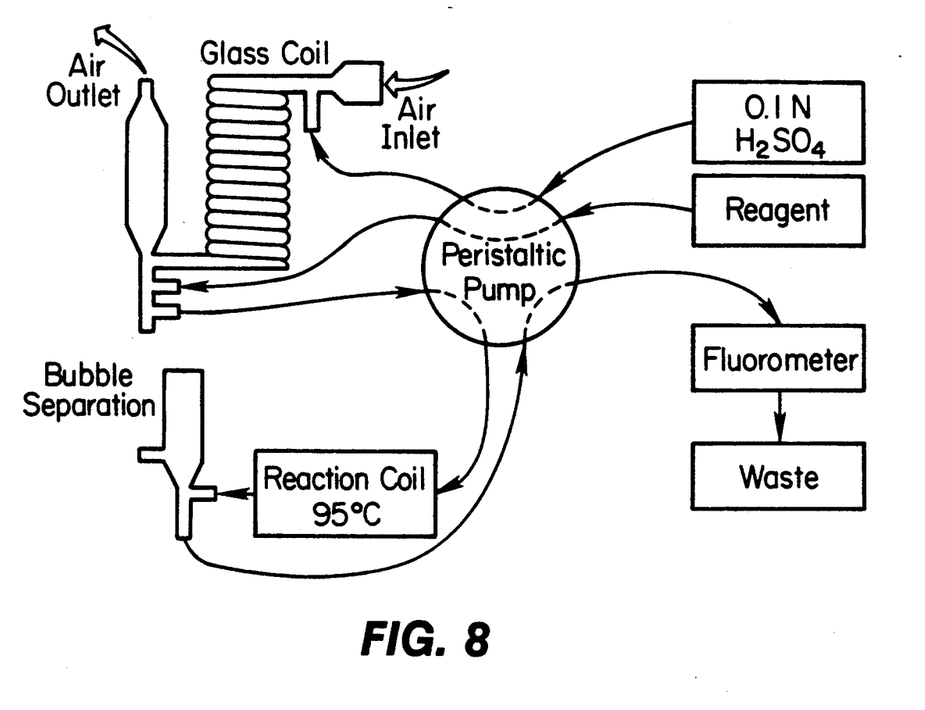
FIG. 8 is a schematic drawing of air and water flow systems in a typical wet chemical monitor for carrying out the present invention.

The increased sensitivity resulting from use of 254 nm excitation implied that the Hantzsch reaction could be used with the glass coil collector to measure HCHO in air at ambient concentrations. The gaseous HCHO instrument was assembled to implement that combination of collector and analytical method. FIG. 8 is a schematic of the instrument. Ambient air is pulled by a pump through the glass scrubbing coil and an air/water separator column before exiting through the pump. Scrubbing solution (0.1N $H_2SO_4$) is pumped into the inlet of the scrubbing coil, and is separated from the air flow at the bottom of the coil, where Hantzsch reagent (2,4-pentanedione in ammonium acetate buffer) is added. The scrubber/reagent mixture is then pumped through a stainless steel coil (1 m of 1/16 in. O.D.) maintained at 95° C. (±1° C.) to promote formation of the fluorescent product DDL. Following removal of bubbles, the solution is pumped through the fluorometer for measurement.

Flow conditions were chosen for the wet chemical detector, and on the basis of those flows reagent concentrations were optimized. The capacity of the concurrent coil scrubber design determined in previous work on HCHO [9] and $H_2O_2$ [18] led to selection of sample air and scrubber solution flow rates of 2.0 L/min and 0.8 cm$^3$/min, respectively. Under such conditions, with the scrubber composition noted above, it was anticipated that collection efficiency for gaseous HCHO would be nearly 100 percent [9]; nevertheless, testing of the collection efficiency was performed and is described later in this section. In order to minimize dilution of the scrubber solution containing collected HCHO, a relatively small flow of relatively concentrated reagent solution was desirable. The optimum reagent concentration was found by selecting a reagent solution flow rate of 0.24 cm$^3$/min, and then testing the sensitivity of the detector for aqueous HCHO as a function of reagent concentration. At this reagent flow rate, residence time of scrubber/regent mixture in the heated stainless reaction coil is 25 seconds, sufficient to bring the reaction close to completion with reasonable reagent concentrations [8]. Results of the test of sensitivity at various reagent concentrations with the chosen flow conditions are shown in FIG. 9.

Figure 9:
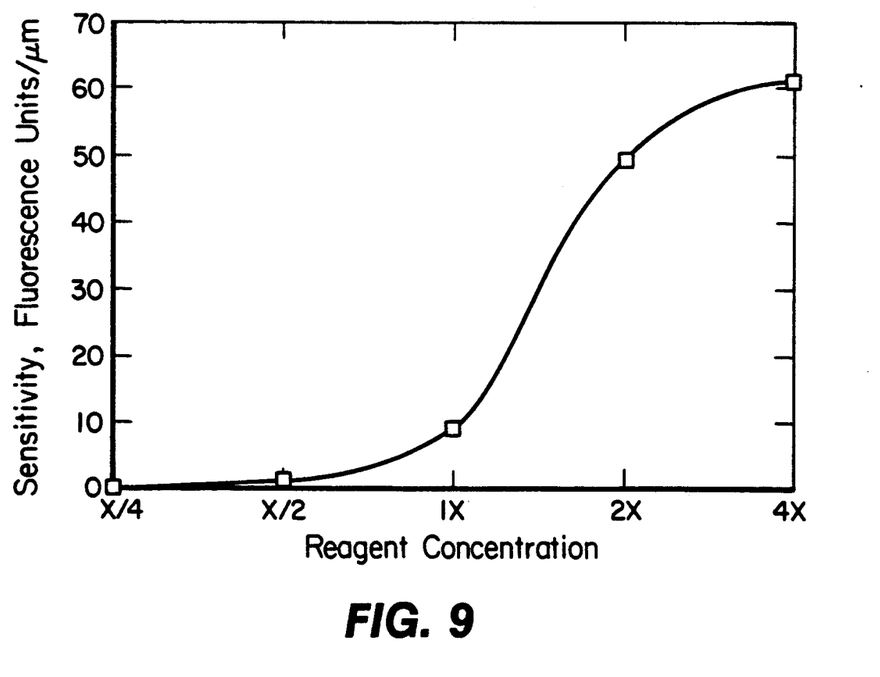
FIG. 9 is a graph of sensitivity against reagent concentration in a typical method according to the present invention.

In FIG. 9 the sensitivity of the improved Hantzsch reaction (in fluorometer display units per micromolar HCHO) is plotted versus the aqueous reagent concentration. The reagent mixture previously used by Dasgupta [7], in a 1:1 scrubber to reagent flow scheme is shown as 1x in FIG. 9; reagent concentrations ¼, ½, twice, and four times as concentrated were also tested. The 1x reagent consists of 154 g ammonium acetate, 3 ml glacial acetic acid, and 0.6 ml 2,4-pentanedione diluted to one liter with water. As FIG. 9 shows, the sensitivity depends greatly on the reagent concentration; this is due to the multistep nature of the Hantzsch reaction, and consequent slow approach to completion at low reagent concentration even at the elevated temperature in the reaction coil. Based on the data of FIG. 9, a reagent concentration of 3x that used by Dasgupta [7] was selected from the wet chemical monitor. More concentrated reagent solutions (e.g., 4x) were found to be more troublesome to make because of difficulty in dissolving the ammonium acetate buffer and provided little increase in sensitivity, and less concentrated reagents (e.g., 2x) give considerably lower sensitivity. Consideration of previous results [8] and additional testing of reagent mixtures disclosed that the 2,4-pentanedione concentration has relatively little effect on the overall sensitivity. Thus the original 3x reagent composition was modified slightly, and the reagent composition adopted for all subsequent work consisted of 231 g ammonium acetate, 4.5 ml glacial acetic acid, and 0.5 ml 2,4-pentanedione diluted to 500 ml with water. This composition is 6M ammonium acetate, 0.16M glacial acetic acid, and $1.0 \times 10^{-2}$M 2,4-pentanedione.

An additional advantage of using a concentrated reagent solution is that the reagent background in the absence of formaldehyde was found to be somewhat lower at higher reagent concentrations. This unexpected observation probably indicates that scattered excitation light is the source of at least some of the reagent background. The reduction in background with more concentrated reagent may be due to greater absorption of the excitation light, or to reduced scattering of excitation light from the fluorescence cell due to changes in the index of refraction of solution in the cell.

The collection efficiency of the glass coil scrubber for HCHO was tested under actual conditions of use, even though previous comparisons with expected Henry's law behavior indicated that equilibrium was achieved, and thus that the efficiency should be nearly 100 percent [15,9]. Testing of collection efficiency was initially done by sampling of room air at various air sample flow rates through the glass coil, starting with a flow rate of 1.0 L/min, at which collection efficiency was known to be close to 100 percent, and continuing up to a flow rate of 3.0 L/min. Assuming that HCHO in room air was present at constant concentration, the response of the wet chemical monitor should increase linearly with air flow rate over the flow range in which 100 percent efficiency is achieved. Performance of this test with room air HCHO concentrations of less than 10 ppbv indicated a collection efficiency of at least 90 percent at the flow rate of 2.0 L/min chosen for the detector. However, the room air HCHO concentration was not sufficiently stable over the duration of the test to allow accurate measurement of the collection efficiency. As a result, a second test was conducted under more controlled conditions.

The second test of HCHO collection efficiency in the glass coil was conducted by supplying a constant flow of 200 cm$^3$/min of air from the porous Teflon tube calibration source, and diluting it in sample flows of 0.86 L/min and 2.0 L/min through the coil. At the former sample flow rate, collection efficiency is known to be essentially 100 percent [9], and since identical amounts of HCHO were provided by the source in each case, comparison of responses indicated relative collection efficiencies at the two air flows. The results of this test are shown in the table. Despite the difference in sampling flow rates of nearly a factor of 2.5, the responses at the two flow rates are nearly identical, indicating the same collection efficiency at 2.0 L/min as at 0.86 L/min. Considering potential sources of error in this test, it is concluded that at the 2.0 L/min sample flow chosen for the wet chemical monitor, the collection efficiency for gaseous formaldehyde is 100 percent, with an uncertainty of about 5 percent.

TABLE

TEST OF COLLECTION EFFICIENCY OF THE GLASS COIL CONCURRENT SCRUBBER[a]

| HCHO Source Air Flow cm$^3$/min | Total Sample Air Flow L/min | Nominal HCHO[b] Concentration ppbv | Response % Full Scale | Collection Efficiency % |
|---|---|---|---|---|
| 200 | 0.86 | 16.0 | 6.9 | 100%[c] |
| 200 | 2.0 | 6.9 | 7.1 | 100% |

[a]Scrubber solution flow 0.8 cm$^3$/min in both cases.
[b]Based on $6.6 \times 10^{-4}$M HCHO in source at 10 C.
[c]Previously established [9].

One of the attractive features of the Hantzsch reaction which led to its selection for this program is its high selectivity toward formaldehyde over other aldehydes [7,8]. This selectivity may result from steric effects associated with the presence of groups other than hydrogen on the aldehyde carbonyl group, in the ring closure reaction forming the fluorescent DDL product. However, all previous interference testing with the Hantzsch reaction had been done using 410 nm excitation. Although loss of specificity of the reaction due to use of 254 nm excitation seemed very unlikely, interference tests were conducted with aqueous solutions of two common possible interferents, acetaldehyde (CH$_3$CHO) and benzaldehyde (C$_6$H$_5$CHO). These tests showed selectivity of the current method toward formaldehyde of greater than 10,000:1 relative to acetaldehyde and greater than 2,000:1 relative to benzaldehyde. The observed selectivity relative to acetaldehyde is consistent with that found previously using 410 nm excitation [8]. These observations indicate that specificity for HCHO is retained following adoption of 254 nm excitation. The previous work [8] also indicates even greater selectivity toward formaldehyde over high aldehydes, acetone, and methanol, than over acetaldehyde. Note that in atmospheric sampling, selectivity toward HCHO will be further improved by the generally lower atmospheric concentrations of other aldehydes relative to formaldehyde, and by the lower solubility and gaseous mobility of other aldehydes, which reduces their efficiency of collection in the scrubber coil.

Other non-aldehyde species which might interfere in the method were not tested in this study, but have been ruled out on the basis of previous studies, or solubility or rate calculations. For example, gaseous $SO_2$ at reasonable atmospheric concentrations (<100 ppbv) cannot interfere by formation of a S(IV)-HCHO adduct, because $SO_2$ solubility will be negligible in the pH 1 scrubber solution, and because the rate of adduct formation is too slow at the concentrations pertaining in the scrubber solution to affect aqueous HCHO concentrations in the brief residence time of solution within the scrubber. Ozone ($O_3$) does not directly interfere in the analysis [7], nor do mixtures of ozone and reactive hydrocarbons produce HCHO in the scrubber coil [9], even at sample air residence times in the collection coil twice as long as those employed here. Thus the wet chemical method appears to be essentially specific for formaldehyde.

The wet chemical HCHO monitor was assembled in an open "bread-board" design for the laboratory testing described above, and was employed in that form for the gaseous sampling described above, and for the extensive field testing described later in this report. At the end of this project, the wet chemical flow system and associated apparatus were packaged into a more compact and easily portable arrangement. The important analytical characteristics of the monitor were the same in both physical configurations. Those characteristics can be summarized as follows: detection limit for aqueous formaldehyde of 0.02 $\mu M$, and for gaseous formaldehyde of 0.2 ppbv, both at a signal/noise ratio of 2; time response consisting of a lag time of less than 2 minutes after a step change in gaseous HCHO at the coil inlet, and rise time (5-95 percent) of about 1 minute; and linearity over the range of at least 0-50 ppbv gaseous formaldehyde, comparable to the full range of expected atmospheric concentrations. These characteristics are sufficient for real-time monitoring of gaseous formaldehyde in the ambient atmosphere, as the field test data which follow will show. These characteristics also compare favorably with those of the previous wet chemical approach using the Hantzsch reaction [7,8], which required the use of a more complicated and less reliable scrubber design.

The primary disadvantage of the present approach is the relatively high reagent background observed with 254 nm excitation, which requires use of a fluorometer capable of substantial blank suppression. The background signal is not a severe limitation, as the present results demonstrate, but it contrasts with the near absence of background fluorescence when the Hantzsch reaction is used with 410 nm excitation. Some reduction in background has been achieved by selection of the commercial source of the 2,4-pentanedione reagent used (Aldrich preferable to Sigma Chemical), indicating that reagent impurities contribute to the background fluorescence. However, purification of the reagents used has not been pursued in this study. It may also be possible to reduce fluorescence background by improved selection of the emission filters used in the fluorometer, beyond the extensive selection process conducted in the present study.

In the compact, portable configuration of the wet chemical HCHO monitor, the glass coil collector, air/water separator, bubble separator, heated reaction coil, peristaltic pump, temperature control circuitry, air flowmeter, and associated plumbing are all housed within a single package of size 16" W×19" H×12" D, weighing about 20 pounds. Only the air sapling pump, fluorometer, and containers for reagents and waste are located external to this package. This arrangement allows for easy access to the peristaltic pump for tubing changes, and yet simplifies and compacts the flow system.

To summarize, a typical method according to the present invention, for monitoring formaldehyde vapor in a gas, comprises directing the gas into contact with an aqueous solution that can dissolve the vapor and thus collect it therein, separating the gas from the solution, reacting the solution with a reagent to form from the collected formaldehyde a derivative that can be excited by radiation at a wavelength in the range of about 230 to 300 nanometers to fluoresce at a substantially different wavelength, irradiating the solution at a wavelength in said range for excitation, and measuring the intensity of the resulting fluorescence.

The fluorescence typically is measured at a wavelength of at least about 450 nanometers; and preferably at a wavelength in the range of about 450 to 550 nanometers; the solution typically being irradiated at a wavelength in the range of about 250 to 260 nanometers. The irradiation and the measurement of fluorescence may be carried out by any suitable means, such as conventional fluorometric means.

For real-time monitoring, the solution should be acidic, preferably having a pH of less than about 2. A typical useful solution comprises sulfuric acid of at least about 0.1N.

Typically the gas and the solution are directed to flow together through a confined sinuous path to provide substantially complete collection of the vapor into the solution; the sinuous path typically being provided by a coil of tubing (typically glass tubing) having an inner wall that does not react with the materials therein. Typically the solution is directed to an end of the coil by pumping means, the gas is admitted to the coil at the same end and is drawn at a constant rate through the coil by vacuum pumping means communicating with the other end of the coil, thereby drawing the solution through the coil also, together with the gas, and causing the vapor to be collected into the solution. Typically the gas and the solution are made to flow together continuously through the coil, and then the gas is separated from the solution by drawing the gas upward while the solution is pulled downward by gravity.

In typical embodiments of the invention, the derivative is formed by the Hantzsch reaction, wherein the reagent comprises 2,4 pentanedione, typically with a pH buffer comprising ammonium acetate and acetic acid, and the derivative that is formed is 3,5-diacetyl 1,4-dihydrolutidine (DDL). The reaction preferably is carried out at elevated temperature, typically at a temperature in the range from about 90 degrees to 100 degrees celsius. Typically bubbles are removed from the solution by gravity before the solution is irradiated.

Typical apparatus for carrying out the method comprises at least a substantial portion of the apparatus disclosed in FIG. 8 and the related description herein, or equivalents thereof.

To measure the concentration of formaldehyde that is already in an aqueous solution, only the last three steps of the above method are needed, namely reacting the solution with a reagent to form from the formaldehyde a derivative that can be excited by radiation at a wavelength in the range of about 230 to 300 nanometers to fluoresce at a substantially different wavelength, irradiating the solution at a wavelength in said range for excitation, and measuring the intensity of the resulting fluorescence.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit or scope of the invention.

I claim:

1. A method of monitoring formaldehyde vapor in a gas, comprising
   directing the gas into contact with an aqueous solution that can dissolve the vapor and thus collect it therein,
   separating the gas from the solution,
   reacting the solution with a reagent to form from the collected formaldehyde a derivative that is excited by radiation at a wavelength in the range of about 230 to 300 nanometers to fluoresce at a substantially different wavelength,
   irradiating the solution at a wavelength in said range for excitation, and
   measuring the intensity of the resulting fluorescence.

2. The method as in claim 1, wherein the fluorescence is measured at a wavelength of at least about 450 nanometers.

3. The method as in claim 1, wherein the fluorescence is measured at a wavelength in the range of about 450 to 550 nanometers.

4. The method as in claim 1, wherein the solution is irradiated at a wavelength in the range of about 250 to 260 nanometers.

5. The method as in claim 1, wherein the irradiation and the measurement of fluorescence are carried out by means comprising conventional fluorometric means.

6. The method as in claim 1, wherein the solution is acidic.

7. The method as in claim 1, wherein the solution has a pH of less than about 2.

8. The method as in claim 1, wherein the solution comprises sulfuric acid of at least about 0.1N.

9. The method as in claim 1, wherein the gas and the solution are directed to flow together through a confined sinuous path to provide substantially complete collection of the vapor into the solution.

10. The method as in claim 9, wherein the sinuous path is provided by a coil of tubing having an inner wall that does not react with the materials therein.

11. The method as in claim 9, wherein the sinuous path is provided by a coil of glass tubing.

12. The method as in claim 10, wherein the solution is directed to an end of the coil by pumping means, the gas is admitted to the coil at the same end and is drawn at a constant rate through the coil by vacuum pumping means communicating with the other end of the coil, thereby drawing the solution through the coil also, together with the gas, and causing the vapor to be collected into the solution.

13. The method as in claim 12, wherein the gas and the solution are made to flow together continuously through the coil.

14. The method as in claim 1, wherein the gas is separated from the solution by drawing the gas upward while the solution is pulled downward by gravity.

15. The method as in claim 1, wherein the derivative is formed by the Hantzsch reaction.

16. The method as in claim 15, wherein the reagent comprises 2,4 pentanedione.

17. The method as in claim 16, wherein the reagent comprises also a pH buffer comprising ammonium acetate and acetic acid.

18. The method as in claim 17, wherein the derivative that is formed is 3,5-diacetyl 1,4-dihydrolutidine (DDL).

19. The method as in claim 15, wherein the reaction is carried out at elevated temperature.

20. The method as in claim 15, wherein the reaction is carried out at a temperature in the range from about 90 degrees to 100 degrees celsius.

21. The method as in claim 15, wherein bubbles are removed from the solution by gravity before the solution is irradiated.

22. A method of measuring the concentration of formaldehyde in an aqueous solution, comprising
   reacting the solution with a reagent to form from the formaldehyde a derivative that is excited by radiation at a wavelength in the range of about 230 to 300 nanometers to fluoresce at a substantially different wavelength,
   irradiating the solution at a wavelength in said range for excitation, and
   measuring the intensity of the resulting fluorescence.

* * * * *